United States Patent [19]

Teed

[11] 4,331,501
[45] May 25, 1982

[54] APPARATUS AND PROCESS FOR SUCCESSIVELY FABRICATING DISPOSABLE DIAPERS HAVING MULTI-LAYER INTERIOR ABSORBENT PADS

[75] Inventor: Richard K. Teed, Greenwood, S.C.

[73] Assignee: Riegel Textile Corporation, New York, N.Y.

[21] Appl. No.: 46,114

[22] Filed: Jun. 6, 1979

[51] Int. Cl.³ ...................... B32B 31/00; B32B 31/04; B32B 5/00; B32B 29/02
[52] U.S. Cl. .................................. 156/383; 156/522; 156/552; 156/563; 156/176; 156/177; 156/213; 128/296; 428/298
[58] Field of Search ............... 156/467, 522, 548, 552, 156/383, 176, 179, 213, 290, 200, 201, 202, 461, 467, 511, 517, 519, 268, 557, 563, 566; 264/258; 425/375; 428/298; 128/284, 286, 287, 290 P, 296; 19/144, 145, 296; 28/107, 109, 112

[56] References Cited

U.S. PATENT DOCUMENTS

| Re. 28,139 | 8/1974 | Gore | 156/467 |
|---|---|---|---|
| 2,600,576 | 6/1952 | Rickard et al. | 128/290 |
| 3,488,778 | 1/1970 | Goujon et al. | 128/284 |
| 3,741,842 | 6/1973 | Joa | 156/213 |
| 3,857,657 | 12/1974 | Teed | 425/375 |
| 3,858,585 | 1/1975 | Chatterjee | 128/290 |
| 3,984,272 | 10/1976 | Teed | 156/548 |
| 3,987,792 | 10/1976 | Hernandez et al. | 128/284 |
| 4,050,462 | 9/1977 | Woon et al. | 128/290 |
| 4,102,340 | 7/1978 | Mesek et al. | 128/286 |

FOREIGN PATENT DOCUMENTS 497334 11/1953 Canada .................................. 156/563

Primary Examiner—Edward C. Kimlin
Assistant Examiner—Louis Falasco
Attorney, Agent, or Firm—Bell, Seltzer, Park & Gibson

[57] ABSTRACT

Apparatus and process for successively fabricating disposable diapers including devices for and the steps of, generally as follows. The components of the diapers are moved in a generally longitudinal path of travel through the apparatus during fabrication of the diapers. Multi-layer interior absorbent pads are produced by fiberizing a first wet-pressed cellulosic fiber sheet and air-laying the fiberized fibers into a bottom layer and fiberizing a second wet-pressed cellulosic fiber sheet and air-laying the fiberized fibers into a top layer in superimposed relation on the bottom layer as the pads are being moved in their longitudinal path of travel. A top cover sheet and a bottom cover sheet are positioned on either side of the multi-layer pad and are secured to each other along longitudinal and transverse edges to form interconnected diapers which are subsequently severed to complete fabrication of the diapers. Preferably, the apparatus forms a diaper of generally hour-glass configuration with elasticized side portions in which strips of elastic are attached to the longitudinal edges at least in the crotch area.

6 Claims, 7 Drawing Figures

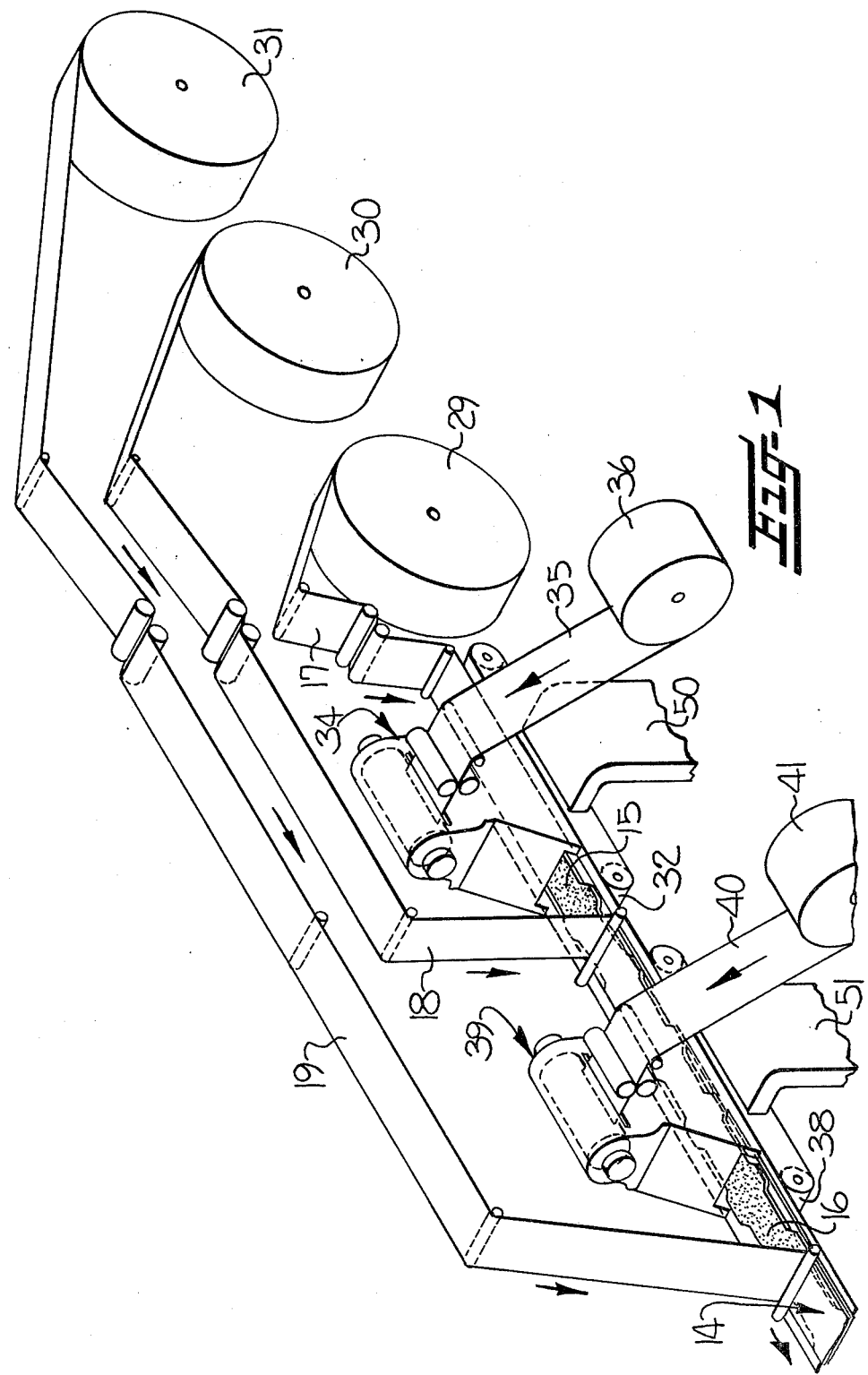

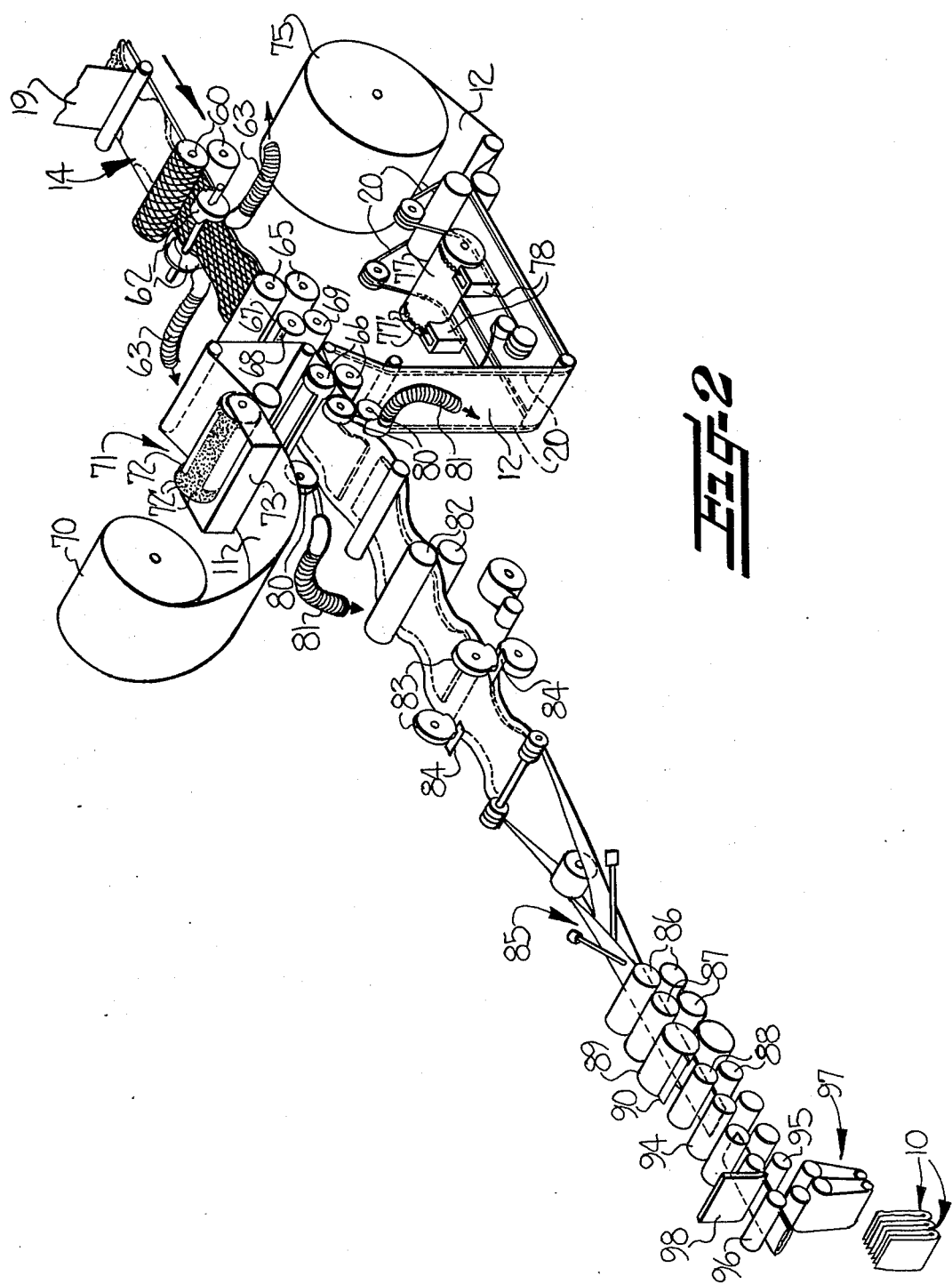

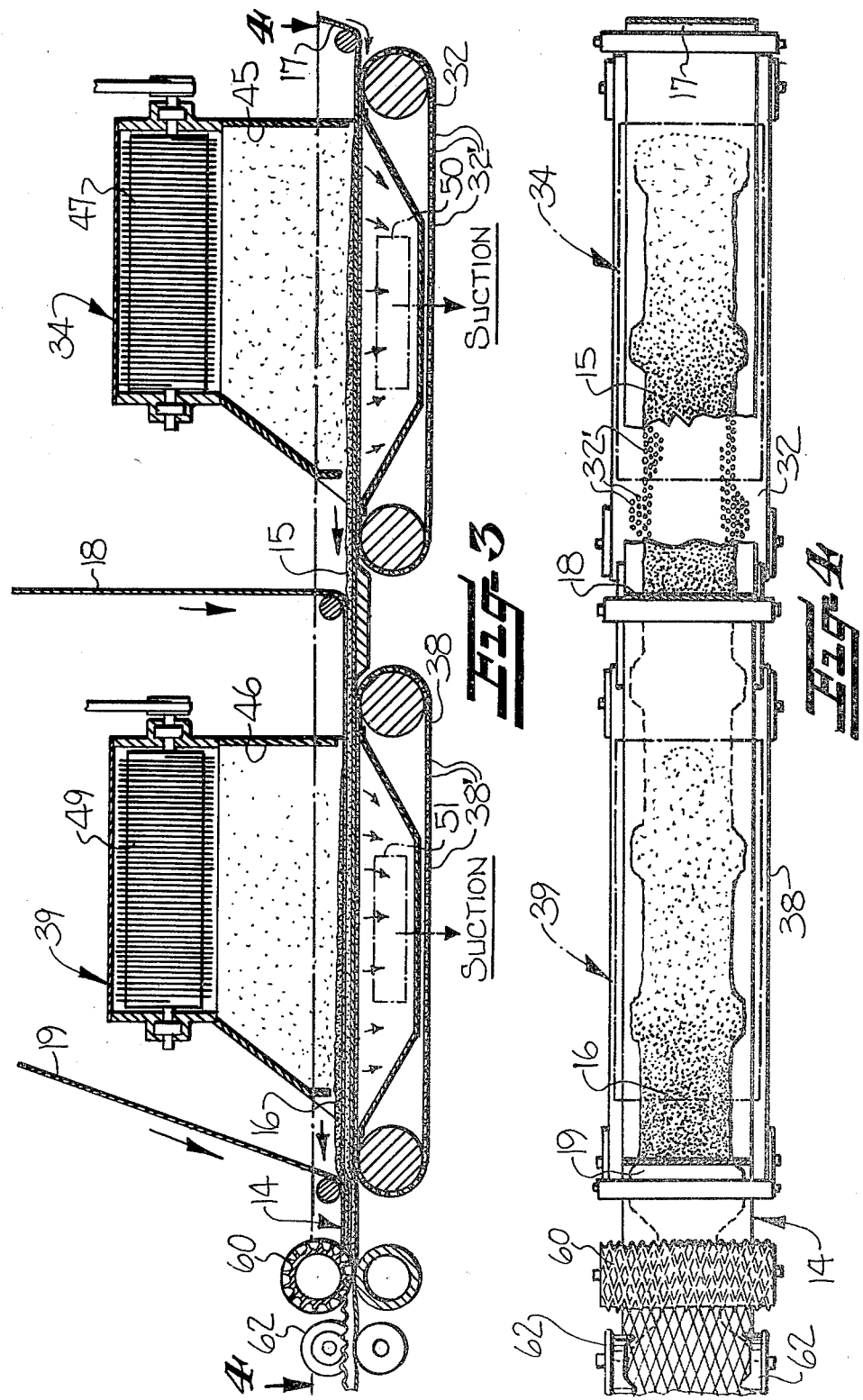

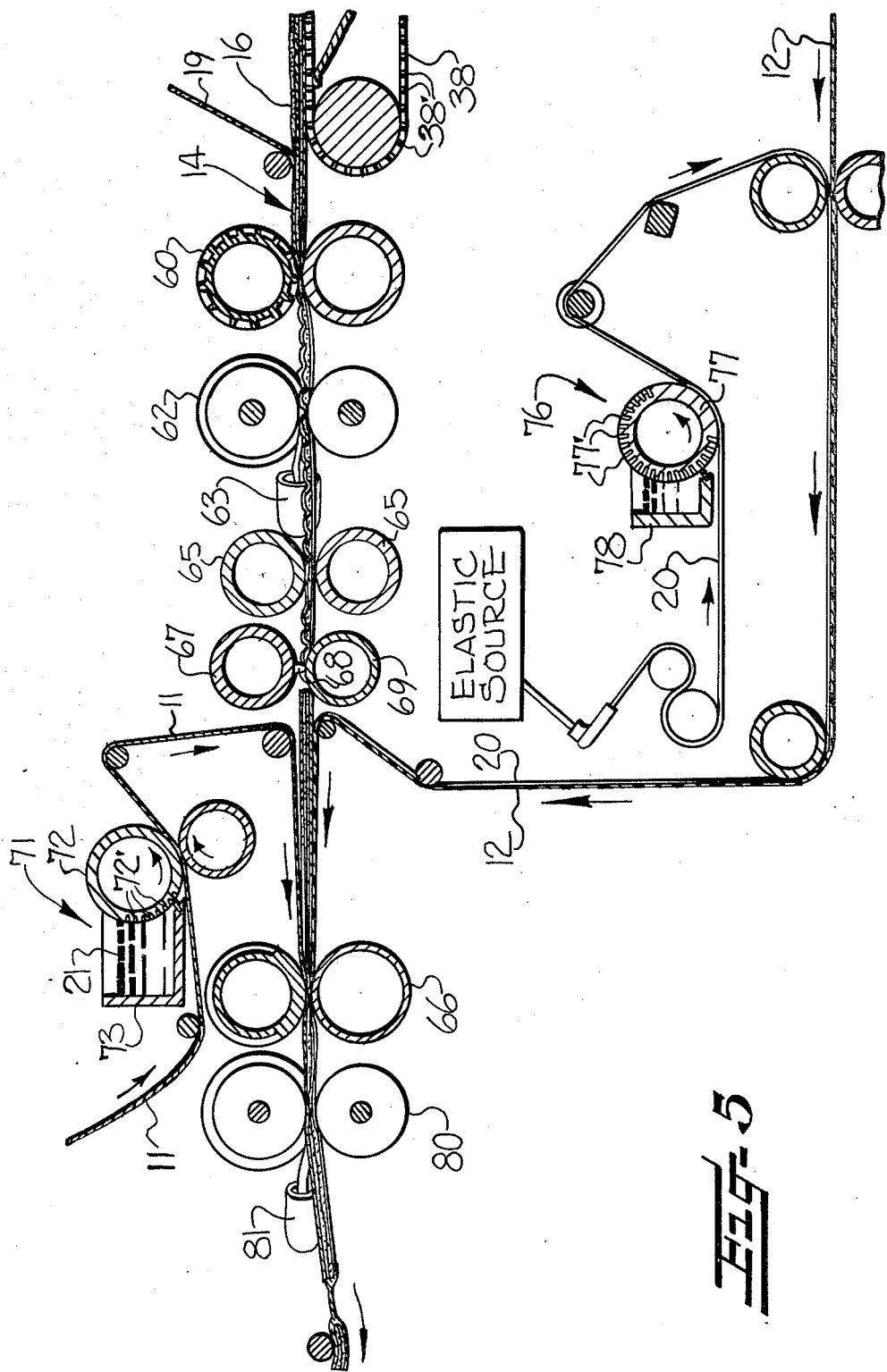

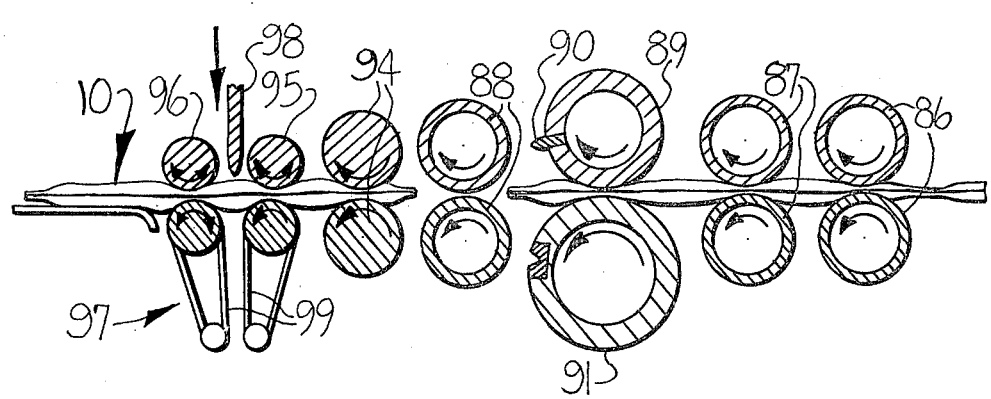
_Fig-6_
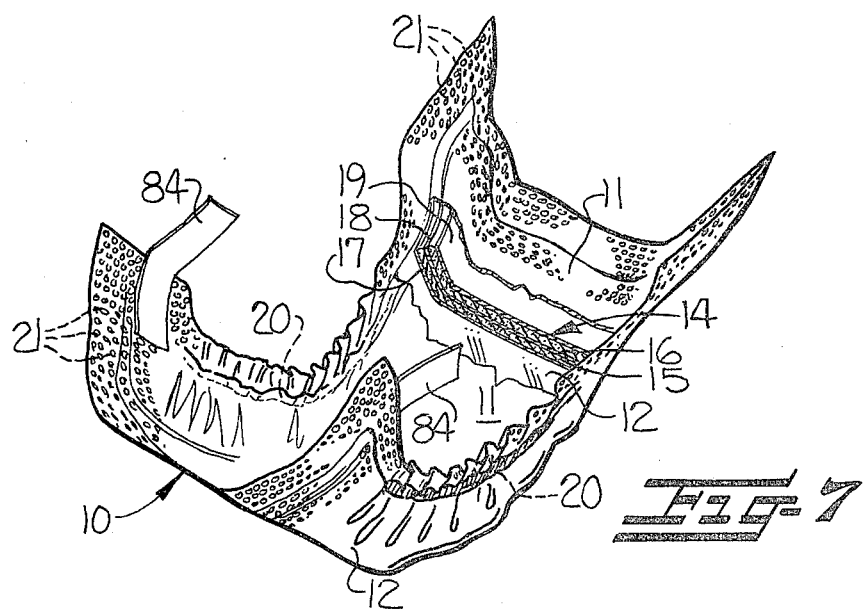
_Fig-7_

APPARATUS AND PROCESS FOR SUCCESSIVELY FABRICATING DISPOSABLE DIAPERS HAVING MULTI-LAYER INTERIOR ABSORBENT PADS

FIELD OF THE INVENTION

This invention relates to an apparatus and process for successively fabricating disposable diapers having multi-layer fluid-absorbent interior pads positioned between fluid-permeable top cover sheets and fluid-impervious bottom cover sheets and, preferably, of generally hour-glass configurations with elasticized side portions.

BACKGROUND OF THE INVENTION

In recent times, disposable diapers, which include fluid-absorbent interior pads positioned between fluid-permeable top cover sheets and fluid-impervious bottom cover sheets, have become increasingly popular. These disposable diapers are fabricated and sold in various shapes, configurations and constructions. Apparatus and processes for successively fabricating such disposable diapers have also been proposed.

Examples of apparatus and processes for successively fabricating two such disposable diapers are disclosed in prior U.S. Pat. No. Re. 28,139, reissued Aug. 27, 1974 and No. 3,984,272, issued Oct. 5, 1976, both of which are assigned to the assignee of the present invention. Both of these prior disposable diaper constructions and the processes and apparatus for fabricating same have been successfully commercially utilized by the assignee of the present invention.

Notwithstanding, there has arisen a need for producing disposable diapers having multi-layer interior absorbent pads, particularly in the recently commercialized disposable diapers of generally hour-glass configuration having elasticized side portions thereon for better conformance to the legs of the wearer. This need, along with the advantages and improvements of such multi-layer interior absorbent pads for disposable diapers and the like, are set forth in co-pending U.S. Patent application Ser. Nos. 046,112 abandoned and 046,113, now U.S. Pat. No. 4,259,958 which were filed concurrently herewith and which are assigned to the assignee of the present invention.

SUMMARY OF THE INVENTION

Accordingly, it is the object of this invention to provide an improved apparatus and process for successively fabricating disposable diapers having muti-layer interior absorbent pads, and preferably, of generally hour-glass configuration with elasticized side portions, which process and apparatus would be adaptable for fabricating disposable diapers with the improved multi-layer interior absorbent pads of the type set forth in the aforementioned co-pending U.S. Patent applications.

In accordance with this invention, it has been found that the above object may be accomplished by providing an apparatus which includes means for and a process which includes the steps of, generally, the following.

Components of the diapers are moved in a generally longitudinal path of travel through the apparatus during fabrication of the disposable diapers. Multi-layer interior absorbent pads are produced including fiberizing a first wet-pressed cellulosic fiber sheet and air-laying the fiberized fibers into a bottom layer while the pads are being moved in the generally longitudinal path of travel, and fiberizing a second wet-pressed cellulosic fiber sheet and air-laying the fiberized fibers into a top layer in superimposed position on the bottom layer for forming multi-layer pads as the pads are being moved in their generally longitudinal path of travel. Preferably, the fiberized fibers are air-laid into bottom and top layers of generally hour-glass configuration for forming hour-glass configured disposable diapers with elasticized side portions.

A continuous fluid-permeable top cover sheet which is somewhat wider than the interior pads is positioned in superimposed relationship on top of the interior pads as they are being moved in their longitudinal path of travel and adhesive is applied to the top cover sheet along longitudinal edges thereof and at spaced locations transversely across the top cover sheet for positioning between spaced-apart interior pads. A continuous fluid-impervious bottom sheet of generally the same width as the top cover sheet is positioned under the interior pads in longitudinal edge alignment with the top sheet. Preferably, elastic strips are intermittently attached to spaced apart sections of each of the longitudinal edges of the bottom cover sheet prior to being positioned under the interior pads for forming the preferred hour-glass configured diaper with elasticized side portions.

The longitudinal edges and the transverse sections of the top cover sheet and bottom cover sheet between the spaced apart interior pads are pressed together with each other for adhesively securing these areas together with the adhesive applied to the top cover sheet for forming a series of interconnected disposable diapers as they are being moved in their longitudinal path of travel. Preferably, intermediate portions of the longitudinal edges of the adhesively secured top cover sheet and bottom cover sheet are intermittently trimmed to form generally hour-glass interconnected disposable diapers. Lastly, the interconnected disposable diapers are intermittently severed transversely across the areas between spaced apart interior pads for forming individual disposable diapers having multi-layer fluid-absorbent interior pads in accordance with this invention.

BRIEF DESCRIPTION OF THE DRAWINGS

Some of the objects and advantages of this invention having been set forth, other objects and advantages will appear when taken in conjunction with the accompanying drawings, in which:

FIGS. 1 and 2 are continuation views schematically illustrating apparatus in accordance with this invention and which is capable of practicing the process of this invention;

FIG. 3 is a sectional view through the fiberizing and air-laying mechanisms illustrated in FIG. 1;

FIG. 4 is a top plan view, partly in section and partly broken away, taken generally along the line 4—4 of FIG. 3;

FIG. 5 is a sectional view taken through the mechanisms for applying the top cover sheet and bottom cover sheet on opposite sides of the interior pads for forming interconnected disposable diapers illustrated in FIG. 2;

FIG. 6 is a sectional view taken through the means for severing the interconnected disposable diapers and for transversely folding such diapers shown in FIG. 2; and FIG. 7 is a view of the preferred disposable diaper of generally hour-glass configuration with elasticized side portions in the relaxed state of the elasticized side por-

DETAILED DESCRIPTION OF INVENTION

Referring now to the drawings, there is schematically illustrated in FIGS. 1-6 apparatus for successively fabricating disposable diapers, preferably of generally hour-glass configuration with elasticized side portions, as shown in FIG. 7, and having multi-layer fluid-absorbent interior pads produced in accordance with this invention.

The apparatus illustrated in FIGS. 1-6 and to be described below has been shown schematically for purposes of simplification of the detailed description and drives and other mechanical details have not been shown inasmuch as they may be easily constructed by one with ordinary skill in the art and do not form a part of the present invention. Also, it is to be understood that certain novel aspects of the apparatus and process in accordance with this invention may be utilized for producing improved multi-layer absorbent pads for use in disposable absorbent articles other than the preferred disposable diaper illustrated in FIG. 7 of hour-glass configuration with elasticized side portions, including the specifically disclosed multi-layer interior absorbent pads of the above two identified co-pending patent applications assigned to the assignee of the present invention.

In accordance with this invention, the apparatus illustrated schematically in FIGS. 1-6 will successively fabricate a disposable diaper, generally indicated at 10 in FIG. 7, which is of generally hour-glass configuration with elasticized side portions. The diaper 10 includes a fluid-permeable top cover sheet 11 of any suitable construction conventionally utilized in disposable diapers for being positioned in contact with the wearer for receiving and passing therethrough body fluids, and a fluid-impervious bottom cover sheet 12 of plastic or other suitable material conventionally utilized in disposable diapers for being positioned away from the wearer for preventing the body fluids of the wearer from passing out of the disposable diaper 10. The diaper 10 further includes a multi-layer fluid-absorbent interior pad 14 positioned between the top cover sheet 11 and the bottom cover sheet 12 for absorbing and containing the body fluids of the wearer. This interior pad preferably includes a bottom layer 15 and a top layer 16 of fiberized cellulosic fibers and sheets of crepe tissue 17, 18 and 19 on each side of and between the top and bottom layers of fiberized fibers 15, 16 for stabilizing the layers of fiberized fibers and the interior pad. The elasticized side portions include elastic strips 20 therein. The longitudinal and transverse edges of the diaper 10 are secured together by adhesive 21 between the top and bottom cover sheets 11, 12 to form an envelope around the interior pad 14.

Referring now to the apparatus and process of this invention, the apparatus includes feeding means which will be specifically identified hereinafter for collectively moving the components of the diapers 10 in a generally longitudinal path of travel through the apparatus during successive fabrication of the disposable diapers 10, as indicated schematically in FIGS. 1 and 2.

Referring firstly to FIG. 1, there is shown means for producing the multi-layer fluid-absorbent interior pads 14. As shown therein, sources of supply 29, 30, 31 are provided for the respective sheets of crepe tissue 17, 18, 19. As may be seen, the bottom sheet of crepe tissue 17 is fed from its source of supply 29 onto a moving conveyor belt 32. This conveyor belt 32 moves through and forms a part of a first fiberizing and air-laying apparatus 34, which may be constructed in accordance with prior U.S. Pat. No. 3,857,657, issued Dec. 31, 1974, and assigned to the assignee of the present invention. This fiberizing and air-laying apparatus 34 receives a sheet 35 of wet-pressed cellulosic fibers from a suitable supply source 36 and mechanically fiberizes the sheet 35 into individual fibers and air-lays the fibers onto the sheet of crepe tissue 17 for forming a first or bottom layer 15 of fiberized fibers. This first layer 15 is of a predetermined configuration, preferably hour-glass.

The superimposed first sheet of crepe tissue 17 and bottom fiberized fiber layer 15 are then fed onto conveyor 38 which forms a part of a second fiberizing and air-laying mechanism 39 which may be constructed like the first fiberizing and air-laying mechanism 34. Prior to entering the second fiberizing and air-laying mechanism 39, the second sheet of crepe tissue 18 is fed from its supply 30 and superimposed onto the bottom fiberized fiber layer 15 so as to stabilize such fiberized fiber layer 15 when fed into the second fiberizing and air-laying mechanism 39.

The second fiberizing and air-laying mechanism 39 receives a sheet 40 of wet-pressed cellulosic fibers from a suitable supply source 41 and mechanically fiberizes the sheet 40 into individual fibers and air-lays the fibers onto the second sheet of crepe tissue 18 for forming a second or top layer 16 of fiberized fibers. This top layer 16 of fiberized fibers is also preferably formed in an hour-glass configuration.

Upon being fed out of the second fiberizing and air-laying mechanism 39, the superimposed first sheet of crepe tissue 17, the bottom layer 15 of fiberized fibers, the second sheet of crepe tissue 18 and the top layer 16 of fiberized fibers receive the third sheet of crepe tissue 19 thereon which is fed from its source of supply 31 into superimposed position thereon for completing formation of the interior absorbent pads 14. As illustrated in the drawings, these interior absorbent pads 14 are preferably in the form of a series of interconnected multi-layer absorbent pads 20.

Referring more specifically to FIGS. 3 and 4, each of the fiberizing and air-laying mechanisms 34, 39 comprise generally an enclosed chamber 45, 46, respectively, which carries a driven, lickerin type of mechanical fiberizing mechanism 47, 49, respectively, in the upper end thereof which contacts the respective sheets of wet-pressed cellulosic fibers 35, 40, which may be obtained from any suitable paper producer, and fiberizes these sheets of fibers into individual fibers in a manner well understood by those with ordinary skill in the art. The individual fibers thus formed are air-laid by gravity onto the respective conveyor belts 32, 38.

These conveyor belts 32, 38 contain groups or series of perforations, indicated at 32', 38', which are arranged in the general configuration desired for the respective top and bottom layers of fiberized fibers 15, 16. In this particular situation, the preferred configuration is interconnected hour-glass configurations, as illustrated in FIGS. 1, 3 and 4. Under the top flight of the respective conveyor belts 32, 38, there is disposed a suction device, 50, 51, respectively, which creates a suction through the perforations 32', 38' in the respective conveyor belts 32, 38 for causing the fiberized fibers being air-laid thereon by gravity to form a predetermined configuration, as more fully explained in the above-mentioned prior U.S.

Pat. No. 3,857,657. The suction created by the suction mechanism 50 will form a suction of the predetermined configuration of the perforations 32' through the tissue sheet 17 and the suction source 51 will form a suction of the predetermined configuration of the perforations 38' through the superimposed first tissue sheet 17, bottom layer 15 of fiberized fibers and second tissue sheet 18.

These interconnected multi-layer absorbent pads 14 may then be fed through a pair of embossing rolls 60 for compressing of the absorbent pads 14 for increasing the moisture wicking action thereof. Upon leaving the embossing rolls 60, the pads 14 are fed through edge trimming devices 62 which intermittently trim the edges of the crepe tissue sheets 17, 18, 19 into generally hourglass configurations of the interconnected absorbent pads 14. Vacuum removal devices 63 may be provided for removing the trimmed material.

The thus formed interconnected multi-layer absorbent pads 14 are then fed through two pairs of driven feed rolls 65, 66 between which is provided a pad severing means in the form of a rotating cutting roll 67 having a knife blade 68 thereon and an anvil roll 69 which operate to intermittently cut the interconnected multi-layer pads 14 transversely for separation of the interconnected pads 14. The driven feed rolls 66 are driven somewhat faster than the driven feed rolls 65 to effect an over feeding of the severed multi-layer absorbent pads 14 for spacing the pads apart in the further fabrication of the disposable diapers, as shown in FIGS. 2 and 5.

Immediately prior to the feed rolls 66, the top cover sheet 11 is fed from a suitable source of supply 70 through a glue applicator device 71 which applies the glue or adhesive 21 in a predetermined pattern transversely across the top cover sheet 11 at spaced locations and along the longitudinal edges of the top cover sheet 11 for purposes of gluing the transverse and longitudinal edges of the ultimately fabricated disposable diaper together, as indicated in FIG. 7. The glue applicator 71 may comprise any suitable glue applicator for the above purposes and as illustrated in FIGS. 2 and 5 may include a driven glue applicator roll 72 having indentations or cups 72' therein which collectively are of the predetermined configuration of the areas for receiving adhesive 21. The applicator roll 72 may pass through an adhesive supply tank 73 for containing a supply of the adhesive 21.

Simultaneously with the above, the bottom cover sheet 12 is fed from a source of supply 75 through a suitable device, schematically illustrated at 76, for adhesively attaching the elastic strips 20 to each longitudinal edge of the bottom cover sheet 12 at spaced locations thereon which ultimately form a crotch area in the fabricated disposable diapers 10.

This device 76 may be of any suitable construction and as schematically illustrated herein comprises two sources of supply of elastic strips 20 which feed the elastic strips 20 in stretched condition past a glue applicator roll 77 having indentations or cups 77' therein which pick up glue from supply tanks 78 and intermittently apply the glue to the surface of the elastic strips 20 as they are passed thereover so that when the elastic strips 20 are fed into position on the bottom cover sheet 12, they will be attached to the cover sheet 12 at spaced apart locations thereon conforming generally to the ultimately fabricated crotch area of the disposable diapers 10.

The bottom cover sheet 12 with the elastic strips 20 thereon is fed into superimposed position under the separated multi-layer absorbent pads 14 and is pressed into contact with the top cover sheet 11 with adhesive 21 thereon by the feed rolls 66 so as to adhesively secure the top cover sheet 11 and the bottom cover sheet 12 to each other along longitudinal edges and transversely between the separated and spaced absorbent pads 14 to form interconnected disposable diapers 10.

The thus formed interconnected diapers 10 are fed through edge trimming devices 80 which trim the longitudinal edges of the adhesively connected top cover sheet 11 and bottom cover sheet 12 to the preferred hour-glass configuration. Vacuum removal means 81 may also be provided with these edge trimming devices 80 for removal of the trimmed material.

The thus formed interconnected diapers 10 are then fed through a pair of feed rolls 82 and past an adhesive tab applying mechanism 83 which applies adhesive tabs 84 at spaced locations on the interconnected diapers 10 for well known purposes in securing the individual diapers 10 to the wearer. The interconnected diapers 10 are then fed through longitudinal folding mechanisms 85 for folding the interconnected diapers along longitudinal fold lines to the desired folded condition. From the folding mechanism 85 the interconnected diapers are fed through a series of pairs of feed rolls 86, 87 and 88 between which is disposed a transverse cutting mechanism composed of a cutting roll 89 having a blade 90 thereon and an anvil roll 91 rotating to cut the interconnected diapers 10 transversely through the transversely adhesively connected portions between spaced apart interior absorbent pads 14 to form individual separated diapers 10.

The thus formed and separated diapers 10 are then fed between a series of guide rolls 94, 95, 96 which are in loose nipping contact with the individual diapers 10 but which do not provide a tight nipping action and allow the diapers 10 to relax to the configuration shown generally in FIG. 7. Between these guide rolls 95, 96, there is disposed a transverse or center-fold mechanism 97 having a folding blade 98 adapted to engage the separated individual diapers 10 transversely across their midpoints and move the diapers 10 downwardly between a set of driven belt conveyors 99 for forming individual folded diapers 10 which may be fed to any suitable packing station, indicated schematically in FIG. 2.

Thus, an improved apparatus and process is provided for successively fabricating disposable diapers, preferably of hour-glass configuration with elasticized side portions, which include a fluid-permeable top cover sheet, a fluid-impervious bottom cover sheet and an interior multi-layer fluid-absorbent pad.

In the drawings and specification, there has been set forth a preferred embodiment of the invention and although specific terms are employed, they are used in a generic and descriptive sense only and not for purposes of limitation.

What is claimed is:

1. An apparatus for successively fabricating disposable diapers, which include a fluid-permeable top cover sheet, a multi-layer fluid-absorbent interior pad positioned under the top cover sheet, and a fluid-impervious bottom cover sheet positioned under the interior pad and secured to the top cover sheet along longitudinal and transverse edges thereon, said apparatus comprising:

feeding means for moving components of the diapers in a generally longitudinal path of travel through said apparatus during fabrication of the disposable diapers;

means for producing spaced-apart multi-layer interior absorbent pads while the pads are being moved in the generally longitudinal path of travel including means for supplying and positioning a first sheet of crepe tissue for longitudinal travel through said apparatus by said feeding means, first means for fiberizing a first wet-pressed cellulosic fiber sheet and for air-laying the fiberized fibers into a bottom layer on top of the first sheet of crepe tissue, means for supplying and positioning a second sheet of crepe tissue on top of the bottom layer of fiberized fibers for longitudinal travel through said apparatus by said feeding means, second means for fiberizing a second wet-pressed cellulosic fiber sheet and for air-laying the fiberized fibers into a top layer in superimposed position on the bottom layer and on top of the second sheet of crepe tissue, and means for supplying and positioning a third sheet of crepe tissue on top of the top layer of fiberized fibers for stabilizing the layers of fiberized fibers and for forming multi-layer pads as the pads are being moved in their generally longitudinal path of travel;

means for supplying and positioning a continuous fluid-permeable top cover sheet which is somewhat wider than the interior pads in superimposed relationship on top of the interior pads as they are being moved in their longitudinal path of travel including means for applying adhesive to the top cover sheet along longitudinal edges thereof and at spaced locations transversely across the top cover sheet for positioning between spaced-apart interior pads;

means for supplying and positioning a continuous fluid-impervious bottom cover sheet of generally the same width as the top cover sheet under the interior pads in longitudinal edge alignment with the top cover sheet;

means for pressing the longitudinal edges and transverse sections of the top cover sheet and bottom cover sheet between the spaced-apart interior pads together with each other for adhesively securing these areas together with the adhesive applied to the top cover sheet for forming a series of interconnected disposable diapers as they are being moved in the longitudinal path of travel; and severing means for intermittently transversely severing the interconnected disposable diapers transversely across the areas between spaced-apart interior pads for forming individual disposable diapers.

2. An apparatus for successively fabricating disposable diapers, wherein the diaper is of generally hour-glass configuration with elasticized side portions and includes a fluid-permeable top cover sheet, a multi-layer fluid-absorbent interior pad positioned under the top cover sheet, and a fluid-impervious bottom cover sheet positioned under the interior pad and secured to the top cover sheet along longitudinal and transverse edges thereon, said apparatus comprising:

feeding means for moving components of the diapers in a generally longitudinal path of travel through said apparatus during fabrication of the disposable diapers;

means for producing spaced-apart multi-layer interior absorbent pads while the pads are being moved in the generally longitudinal path of travel including means for supplying and positioning a first sheet of crepe tissue for longitudinal travel through said apparatus by said feeding means, first means for fiberizing a first wet-pressed cellulosic fiber sheet and for air-laying the fiberized fibers into a bottom layer on top of the first sheet of crepe tissue, means for supplying and positioning a second sheet of crepe tissue on top of the bottom layer of fiberized fibers for longitudinal travel through said apparatus by said feeding means, second means for fiberizing a second wet-pressed cellulosic fiber sheet and for air-laying the fiberized fibers into a top layer in superimposed position on the bottom layer and on top of the second sheet of crepe tissue, and means for supplying and positioning a third sheet of crepe tissue on top of the top layer of fiberized fibers for stabilizing the layers of fiberized fibers and for forming multi-layer pads as the pads are being moved in their generally longitudinal path of travel;

means for supplying and positioning a continuous fluid-permeable top cover sheet which is somewhat wider than the interior pads in superimposed relationship on top of the interior pads as they are being moved in their longitudinal path of travel including means for applying adhesive to the top cover sheet along longitudinal edges thereof and at spaced locations transversely across the top cover sheet for positioning between spaced-apart interior pads;

means for supplying and positioning a continuous fluid-impervious bottom cover sheet of generally the same width as the top cover sheet under the interior pads in longitudinal edge alignment with the top cover sheet including means for intermittently adhesively attaching elastic strips to each of the longitudinal edges of the bottom cover sheet prior to being positioned under the interior pads;

means for pressing the longitudinal edges of the top cover sheet and bottom cover sheet with elastic strips thereon and the transverse sections of the top cover sheet and the bottom cover sheet between the spaced-apart interior pads together with each other for adhesively securing these areas together with the adhesive applied to the top cover sheet for forming a series of interconnected disposable diapers as they are being moved in the longitudinal path of travel;

edge trimming means for intermittently trimming intermediate portions of the longitudinal edges of the adhesively secured top cover sheet and bottom cover sheet to form generally hour-glass interconnected disposable diaper; and severing means for intermittently transversely severing the interconnected disposable diapers transversely across the areas between spaced-apart interior pads for forming individual disposable diapers.

3. In an apparatus for successively fabricating disposable diapers, wherein the diaper includes a fluid-permeable top cover sheet, a fluid-absorbent interior pad positioned under the top cover sheet, and a fluid-impervious bottom cover sheet positioned under the interior pad and secured to the top cover sheet along longitudinal and transverse edges thereon; the improvement of means for producing multi-layer interior absorbent pads comprising:

feeding means for moving components of the multi-layer absorbent pads in a generally longitudinal path of travel through said apparatus during fabrication of the absorbent pads;

means for supplying and positioning a first sheet of crepe tissue for longitudinal travel through said apparatus by said feeding means;

first means for fiberizing a first wet-pressed cellulosic fiber sheet and for air-laying the fiberized fibers into a bottom layer on top of the first sheet of crepe tissue while the pads and sheet of crepe tissue are being moved in the generally longitudinal path of travel;

means for supplying and positioning a second sheet of crepe tissue on top of the bottom layer of fiberized fibers for longitudinal travel through said apparatus by said feeding means;

second means for fiberizing a second wet-pressed cellulosic fiber sheet and for air-laying the fiberized fibers into a top layer on top of the second sheet of crepe tissue and in superimposed position on the bottom layer of fiberized fibers while the pads are being moved in the generally longitudinal path of travel; and means for supplying and positioning a third sheet of crepe tissue on top of the top layer of fiberized fibers for stabilizing the layer of fiberized fibers and the interior pads.

4. An apparatus, as set forth in claim 1 or 2, in which said means for producing the spaced-apart multi-layer interior pads further includes means for air-laying the fiberized fibers in the form of interconnected pads of predetermined configuration, means for transversely severing the interconnected pads into individual pads while they are being moved in the generally longitudinal path of travel, and means for over feeding the severed individual interior pads while they are being moved in their longitudinal path of travel for spacing apart the severed individual pads.

5. An apparatus, as set forth in claim 1 or 2, in which said first and second fiberizing and air-laying means each further comprise generally enclosed, stationary chamber means having an open bottom and a slot in the upper portion thereof to receive a sheet of wet-pressed fibers, rotatably mounted and driven licker-in type fiberizing means mounted in the upper portion of said chamber means for contacting the sheet of wet-pressed pulp fibers and fiberizing the sheet into substantially individual fibers, driven conveyor means having perforations therein corresponding to the desired configuration of the interior pads being formed and being positioned for movement along said open bottom end of said chamber means directly below said fiberizing means for receiving the sheet of crepe tissue and fiberized fibers on the upper surface thereof and conveying the sheet of crepe tissue and fiberized fibers out of said chamber means, and stationary suction means positioned at the lower surface of said conveyor means for creating a suction through said perforations and sheet of crepe tissue for causing the fibers to be pulled to said groups of perforations to define the desired shape of said pads.

6. In an apparatus, as set forth in claim 3, in which said first and second fiberizing and air-laying means each further comprise generally enclosed, stationary chamber means having an open bottom and a slot in the upper portion thereof to receive a sheet of wet-pressed fibers, rotatably mounted and driven licker-in type fiberizing means mounted in the upper portion of said chamber means for contacting the sheet of wet-pressed pulp fibers and fiberizing the sheet into substantially individual fibers, driven conveyor means having perforations therein corresponding to the desired configuration of the interior pads being formed and being positioned for movement along said open bottom end of said chamber means directly below said fiberizing means for receiving the sheet of crepe tissue and fiberized fibers on the upper surface thereof and conveying the sheet of crepe tissue and fiberized fibers out of said chamber means, stationary suction means positioned at the lower surface of said conveyor means for creating a suction through said perforations and sheet of crepe tissue for causing the fibers to be pulled to said groups of perforations to define the desired shape of said pads.

* * * * *